United States Patent [19]

Katsumata et al.

[11] Patent Number: 4,775,623

[45] Date of Patent: Oct. 4, 1988

[54] PROCESS FOR PRODUCING L-ARGININE

[75] Inventors: Ryoichi Katsumata; Haruhiko Yokoi, both of Machida; Tetsuo Oka, Yokohama, all of Japan

[73] Assignee: Kyowa Khkko Kogyo Co., Ltd., Tokyo, Japan

[21] Appl. No.: 646,512

[22] Filed: Aug. 31, 1984

[30] Foreign Application Priority Data

Sep. 24, 1983 [JP] Japan .................... 58-176758

[51] Int. Cl.[4] .................. C12P 13/10; C12N 15/00; C12N 1/20; C12R 1/15; C12R 1/13
[52] U.S. Cl. ............................ 435/114; 435/172.3; 435/253; 435/843; 435/840; 935/60; 935/72
[58] Field of Search ............. 435/114, 172.3, 253, 435/317, 840, 843; 935/29, 60, 72

[56] References Cited

U.S. PATENT DOCUMENTS

| 4,430,430 | 2/1984 | Momose et al. ................. 435/114 |
| 4,495,283 | 1/1985 | Araki ............................... 435/107 |

FOREIGN PATENT DOCUMENTS

| 0553843 | 5/1986 | Australia . |
| 0058889 | 9/1982 | European Pat. Off. ........... 935/29 |
| 0063763 | 11/1982 | European Pat. Off. ........... 435/843 |
| 0066129 | 12/1982 | European Pat. Off. . |
| 0071023 | 2/1983 | European Pat. Off. . |
| 0082485 | 6/1983 | European Pat. Off. . |
| 0088166 | 9/1983 | European Pat. Off. . |
| 0093611 | 11/1983 | European Pat. Off. . |
| 0131171 | 1/1985 | European Pat. Off. . |
| 2076853 | 12/1981 | United Kingdom . |

OTHER PUBLICATIONS

Nakayama, K. in *Prescott and Dunn's Industrial Microbiology*, (G. Reed, Ed.), AVI Publishing Co., 4th Ed., pp. 748–749.
Udaka, S., *J. Bacteriology*, vol. 91, pp. 617–621, 1966.
Crabeel, M. et al., *Gene*, vol. 5, pp. 207–231, 1979.
Bachman, B. et al., *Microbiol. Reviews*, vol. 44, pp. 1–3, 1980.

*Primary Examiner*—Thomas G. Wiseman
*Assistant Examiner*—Jayme A. Huleatt
*Attorney, Agent, or Firm*—Fitzpatrick, Cella, Harper & Scinto

[57] ABSTRACT

Disclosed is a process for producing L-arginine by transforming a host microorganism belonging to the genus Corynebacterium or Brevibacterium with a recombinant DNA of a DNA fragment containing a gene involved in the biosynthesis of L-arginine and a vector DNA, culturing the transformant in a nutrient medium, accumulating L-arginine in the culture medium and recovering L-arginine therefrom.

6 Claims, 1 Drawing Sheet

PROCESS FOR PRODUCING L-ARGININE

BACKGROUND OF THE INVENTION

For the direct production of L-arginine by fermentation methods using glutamic acid-producing microorganisms belonging to the genus Corynebacterium or Brevibacterium, the method using L-arginine-producing mutant strains derived from wild-type strains are known.

As the L-arginine-producing mutant strains, those resistant to amino acid analogs or those having both characteristics resistant to amino acid analogs and requiring nucleic acid bases for their growth are described in Agr. Biol. Chem., 36, 1675–1684 (1972) and Japanese Published Examined Patent Application Nos. 37235/79 and 150381/82.

The present inventors have studied the production of L-arginine using a microorganism belonging to the genus Corynebacterium or Brevibacterium by recombinant DNA technology different from the conventional mutational breeding technology for the purpose of improving the L-arginine productivity. As the result, the present inventors have found that a microorganism harboring a recombinant DNA of a gene encoding for the enzyme involved in the biosynthesis of L-arginine and a vector plasmid of the microorganism belonging to the genus Corynebacterium or Brevibacterium is superior in production of L-arginine than a microorganism which does not harbor such recombinant.

The fact that the introduction of a recombinant DNA containing a gene encoding for the enzyme involved in arginine biosynthesis into L-arginine-nonproducing microorganism belonging to the genus Corynebacterium or Brevibacterium confers L-arginine productivity on the microorganism has been found first by the present inventors.

SUMMARY OF THE INVENTION

This invention relates to a process for producing L-arginine by a novel expression method of a gene. More specifically, the present invention is a process for producing L-arginine by transforming a host microorganism belonging to the genus Corynebacterium or Brevibacterium with a recombinant DNA comprising a DNA fragment containing a gene encoding for the enzyme involved in the biosynthesis of L-arginine and a vector DNA, culturing the transformant in a nutrient medium, accumulating L-arginine in the culture medium and recovering L-arginine therefrom.

DESCRIPTION OF THE INVENTION

Figure 1:
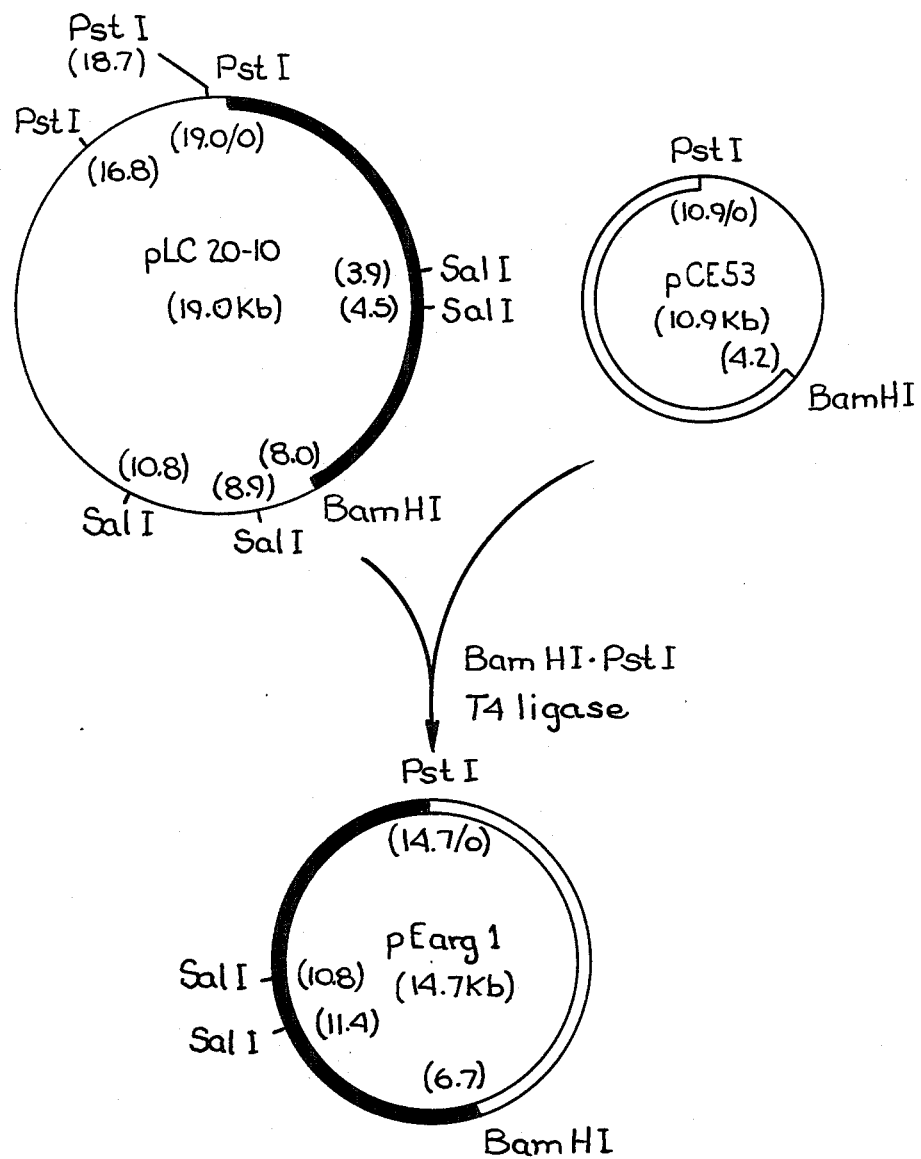
FIG. 1 illustrates the process for construction of plasmid pEarg1. The restriction endonucleases used in the preparation of the cleavage map are PstI, BamHI and SalI. Molecular weight of the plasmid is indicated as Kilobase (Kb).

The present invention provides a process for producing L-arginine by culturing in a medium a transformant which is obtained by transforming a microorganism belonging to the genus Corynebacterium or Brevibacterium with a recombinant DNA comprising a DNA fragment containing a gene encoding for the enzyme involved in the biosynthesis of L-arginine and a vector DNA.

As the host microorganism belonging to the genus Corynebacterium or Brevibacterium, all of the microorganisms known as so-called glutamic acid-producing microorganisms are applicable. The following are examples of suitable host microorganisms.

Corynebacterium glutamicum: ATCC 13032
Corynebacterium acetoacidophilum: ATCC 13870
Corynebacterium herculis: ATCC 13868
Corynebacterium lilium: ATCC 15990
Brevibacterium divaricatum: ATCC 14020
Brevibacterium flavum: ATCC 14067
Brevibacterium immariophilium: ATCC 14068
Brevibacterium lactofermentum: ATCC 13869
Brevibacterium thiogenitalis: ATCC 19240

As the host, either wild-type strains which do not produce L-arginine or strains which already have an ability to produce L-arginine can be employed. As the latter strains, amino acid analog-resistant mutant strains are used.

As the enzyme involved in the biosynthesis of L-arginine, N-acetylglutamate synthetase, N-acetylglutamokinase, N-acetylglutamate-$\gamma$-semialdehyde dehydrogenase, N-acetylornithine-$\delta$-aminotransferase, acetylornithine deacetylase, N-acetylglutamate-acetylornithine acetyltransferase, ornithine carbamoyltransferase, arginosuccinate synthetase, argininosuccinase, and the like [Agr. Biol. Chem., 43, 1899–1903 (1979)] are mentioned.

As the gene encoding for the enzymes involved in the biosynthesis of L-arginine, the DNA carrying the genetic information of at least one of these enzymes is used. Any DNA may be used so long as it is derived from prokaryotes, eukaryotes, bacteriophages, viruses or plasmids. The genes involved in the biosynthesis of L-arginine derived from prokaryotes, bacteria such as the microorganisms belonging to the genus Escherichia, Corynebacterium, Brevibacterium, Microbacterium, Bacillus, Stapylococcus, Streptococcus or Serratia are preferable and especially the genes derived from arginine-producing mutants belonging to such bacteria are preferably used. The gene responsible for the biosynthesis of arginine of Escherichia coli K-12 is a preferable example.

As the vector used to incorporate the DNA, the plasmids constructed by the present inventors, pCG1, pCG2, pCG4, pCG11, pCE53, pCE54 and pCB101 are preferably used. The methods of producing these vectors are described in Japanese Published Unexamined Patent Application Nos. 134500/82, 183799/82, 35197/83 and 105999/83 and Japanese Patent Application No. 25398/83.

The recombinant DNA of the donor DNA encoding for the enzyme involved in the biosynthesis of arginine and the vector DNA is obtained by the recombinant DNA technology which comprises cleaving in vitro both DNAs with restriction enzymes, recombining the cleaved DNAs by DNA ligase, transforming a mutant strain belonging to the genus Corynebacterium or Brevibacterium which is defective in the gene encoding for the enzyme involved in the biosynthesis of arginine with the ligation mixture, and selecting the transformants wherein the defective phenotype is restored. The method of recombinant DNA technology is described in Japanese Published Unexamined Patent Application Nos. 186492/82 and 186489/82.

Instead of cloning the recombinant DNA directly in a microorganism belonging to the genus Corynebacterium or Brevibacterium, the recombinant DNA can also be obtained by using another well established host-vector system as exemplified with *Escherichia coli* system. That is, recombinant DNAs can be obtained by the method which comprises transforming an *Escherichia coli* mutant which lacks the gene encoding for the enzyme involved in the biosynthesis of arginine with the in vitro ligation mixture of the donor DNA encoding for the enzyme involved in the biosynthesis of arginine and the vector DNA, and selecting transformants wherein the defective phenotype is restored. The cloned DNA and a vector DNA of the microorganism belonging to the genus Corynebacterium or Brevibacterium are cleaved with a restriction enzyme and religated with DNA ligase. A mutant strain belonging to the genus *Escherichia coli* and defective in the gene encoding for the enzyme involved in the biosynthesis of arginine with the ligation mixture is transformed, and the transformants which have a selective marker derived from Corynebacterium or Brevibacterium species and restored the defective phenotype are selected.

Selection of the recombinant between the cloned DNA in the *Escherichia coli* host and a vector DNA derived from the genus Corynebacterium or Brevibacterium is also carried out, without using *Escherichia coli*, by transforming a Corynebacterium or Brevibacterium mutant strain which is defective in a gene encoding for the enzyme involved in the biosynthesis of arginine and selecting the transformant in which the defective phenotype is restored.

As a DNA containing a gene responsible for the biosynthesis of arginine used in the present invention, genes located convergently at around 90 minutes on the chromosomal map of *Escherichia coli* K-12, containing the genes encoding for acetylornithine deacetylase (argE), N-acetylglutamate-γ-semialdehyde dehydrogenase (argC), N-acetylglutamokinase (argB) and argininosuccinase (argH) [Glansdorff, N.: Genetics, 51, 167 (1965)] are mentioned.

The present invention is explained in more detail using pEarg1 which is a recombinant plasmid containing the DNA of *Escherichia coli* K-12 genes responsible for the biosynthesis of arginine.

pEarg1 can be obtained as a recombinant of pLC20-10 and pCE53 using a host-vector system of *Escherichia coli*. pLC20-10 is obtained from the gene bank of *Escherichia coli* K-12 and is known as a plasmid carrying the genes responsible for the biosynthesis of arginine described above [Clarke, L. et al.: Cell, 9, 91 (1976)].

pCE53 is a plasmid constructed by the present inventors and described in Japanese Patent Application No. 25398/83. It is prepared by inserting a linearized *Escherichia coli* vector plasmid pGA22 [An. G. et al.: J. Bacteriol., 140, 400 (1979)] which is cut with BamHI at one of the two BamHI cleavage sites into the unique BglII cleavage site of plasmid pCG1 (Japanese Published Unexamined Patent Application No. 134500/82) isolated from *Corynebacterium glutamicum* 225-57 (ATCC 31808, FERM-P 5865) using the same cohesive ends of both fragments. pCE53 is replicable in both the glutamic acid-producing microorganisms such as those belonging to the genus Corynebacterium or Brevibacterium and the microorganisms belonging to *Escherichia coli* and carries the kanamycin-resistance gene as a selective marker. pLC20-10 is isolated from pLC20-10-carrying *Escherichia coli* by a conventional method [An, G. et al.: J. Bacteriol., 140, 400 (1979)]. pCE53 is isolated from the cultured cells of pCE53-carrying *Corynebacterium glutamicum* L-22 by the same method as described in Japanese Published Unexamined Patent Application No. 186492/82.

Both plasmids are double-digested with PstI and BamHI and the digests are treated with T4 ligase. *Escherichia coli* CH754, a derivative of K-12, which requires methionine, tryptophan and arginine due to the defective mutation of argininosuccinase (argH), [Clarke L. and J. Carbon: Cell, 9, 91–99 (1976)], is transformed with the DNA mixture by a conventional method [Dagert, M. and S. D. Ehrlich: Gene, 6, 23–28 (1979)]. Transformants grown on a minimal medium containing kanamycin and requiring nutrients except arginine are selected. Plasmids are isolated from cultured cells of the selected arginine-nonrequiring transformant by the conventional method [An, G. et al.: J. Bacteriol., 140, 400 (1979)]. The DNA fragment inserted in pCE53 is detected by the double digestion with PstI and BamHI and the analysis by agarose gel electrophoresis. pEarg1 illustrated in FIG. 1 is the thus obtained plasmid wherein a DNA fragment of 8.0 Kb having PstI and BamHI cleavage ends is inserted in pCE53. The process for producing pCE53 is also illustrated in FIG. 1.

When *Escherichia coli* CH754 is retransformed with pEarg1, arginine requirement is restored accompanied by kanamycin-resistant phenotype. Through transformation, pEarg1 also restores arginine requirement of *Escherichia coli* CSR603 which is a derivative of K-12 strain and requires threonine, leucine, proline, thiamine and arginine due to the defective mutation of acetylornithine deacetylase (argE) [Sancar A. and C. S. Rupert: Mutat. Res., 51, 139–143 (1978)].

Genes responsible for the synthesis of arginine located at around 90 minutes on the chromosomal map of *Escherichia coli* K-12 are known to be in the order of argE, argC, argB and argH [Glansdorff, N.: Genetics, 51, 167 (1965)]. It is sure that pEarg1 which can restore argE and argH contains argC and argB.

Since pEarg1 has a replication function derived from pCG1 and is stably inherited in the microorganisms of the genus Corynebacterium or Brevibacterium, the expression in a microorganism of the genus Crynebacterium or Brevibacterium of the *Escherichia coli* gene which is responsible for the biosynthesis of arginine and is contained in pEarg1 can be detected by the restoration of arginine requirement on the introduction of the gene into an arginine-requiring mutant of the genus Corynebacterium or Brevibacterium which is defective in the genes corresponding to the gene responsible for the biosynthesis of arginine in pEarg1. For the detection, *Corynebacterium glutamicum* LA291 requiring arginine for its growth is transformed.

*Corynebacterium glutamicum* LA291 is a mutant which is derived by a conventional mutagenesis from lysozyme-sensitive mutant strain L-15 (Japanese Published Unexamined Patent Application No. 186489/82) derived from *Corynebacterium glutamicum* ATCC 31833 (Japanese Published Unexamined Patent Application No. 186492/82) and which requires arginine. It is assumed that the defective mutation depends on the loss of arginosuccinate synthetase corresponding to argG of *Escherichia coli* or argininosuccinase corresponding to argH of *Escherichia coli* since growth of the mutant does not respond to citrulline which is a precursor two steps before arginine on the pathway of arginine biosynthesis.

Transformation is carried out by the transformation method using protoplasts of the genus Corynebacterium or Brevibacterium described in Japanese Published Unexamined Patent Application Nos. 186492/82 and 186489/82.

Corynebacterium glutamicum LA291 is transformed by the method using protoplasts as described above. The colony grown on a regeneration medium containing kanamycin obtains simultaneously arginine-non-requiring phenotype and harbors pEarg1 characterized by cleavage pattern for various restriction endonucleases. Therefore, it is manifest that arginine-requirement of Corynebacterium glutamicum LA291 is restored by pEarg1. It is proved that an Escherichia coli-derived gene responsible for the biosynthesis of arginine in pEarg1 is expressible in Corynebacterium glutamicum LA291.

An L-arginine producing strain belonging to the genus Corynebacterium or Brevibacterium and harboring pEarg1 is obtained by transforming protoplasts of the genus Corynebacterium or Brevibacterium with pEarg1 and selecting by kanamycin resistance marker by the same method as described above.

The presence of pEarg1 in the transformant is detected by isolating the plasmid from the transformant, digesting the plasmid with various restriction enzymes and analyzing DNA fragments by agarose gel electrophoresis as described above. Practical embodiments of L-arginine-producing strains are Corynebacterium glutamicum K46 (FERM BP-356) which is prepared by introducing pEarg1 into Corynebacterium glutamicum ATCC13032, Corynebacterium herculis K47 (FERM BP-367) which is prepared by introducing pEarg1 into Corynebacterium herculis ATCC13868 and Brevibacterium flavum K48 (FERM BP-357) which is prepared by introducing pEarg1 into Brevibacterium flavum ATCC14067.

These strains were deposited with the Fermentation Research Institute, Agency of Industrial Science and Technology, Ibaraki, Japan on Sept. 12, 1983 and Sept. 21, 1983.

Production of L-arginine by the transformant harboring pEarg1 is carried out by a conventional fermentation method used in the production of L-arginine.

That is, the transformant is cultured in a conventional medium containing carbon sources, nitrogen sources, inorganic materials, amino acids, vitamins, etc. under aerobic conditions, with adjustment of temperature and pH. L-Arginine, thus accumulated in the medium, is recovered.

As the carbon source, various carbohydrates such as glucose, glycerol, fructose, sucrose, maltose, mannose, starch, starch hydrolyzate and molasses, polyalcohols and various organic acids such as pyruvic acid, fumaric acid, lactic acid and acetic acid may be used. Hydrocarbon and alcohols are employed in the strains which can assimilate them. Blackstrap molasses is most preferably used.

As the nitrogen source, ammonia, various inorganic or organic ammonium salts such as ammonium chloride, ammonium sulfate, ammonium carbonate and ammonium acetate, urea, and nitrogenous organic substances such as peptone, NZ-amine, meat extract, yeast extract, corn steep liquor, casein hydrolyzate, fish meal or its digested product, defatted soybean or its digested product and chrysalis hydrolyzate are available.

As the inorganic materials, potassium dihydrogenphosphate, dipotassium hydrogenphosphate, ammonium sulfate, ammonium chloride, magnesium sulfate, sodium chloride, ferrous sulfate, manganese sulfate and calcium carbonate may be used. Vitamins and amino acids required for the growth of microorganisms may not be added, provided that they are supplied with other components mentioned above.

Culturing is carried out under aerobic conditions with shaking or aeration-agitation. Culturing temperature is preferably 20° to 40° C. The pH of the medium during culturing is maintained around neutral. Culturing is continued until a considerable amount of L-arginine is accumulated, generally for 1 to 5 days.

After completion of the culturing, cells are removed and L-arginine is recovered from the culture liquor by conventional manners such as treatment with active carbon or ion exchange resin.

Higher amount of L-arginine is obtained using the strains of the genus Corynebacterium or Brevibacterium harboring pEarg1 compared with the strains which do not contain pEarg1.

In the present specification, wild-type strains of the genus Corynebacterium or Brevibacterium are used to show the contribution of pEarg1 to the L-arginine production. However, introduction of pEarg1 into an arginine-producing mutant leads to higher productivity of arginine.

The usefulness of the present invention lies in the fact that, in an expressible form, introduction of the recombinant DNA constructed with a gene involved in the biosynthesis of arginine and a vector DNA of the genus Corynebacterium or Brevibacterium into a microorganism belonging to the genus Corynebacterium or Brevibacterium can give or improve L-arginine productivity. The example of using the genes responsible for the biosynthesis of arginine of Escherichia coli is provided in the present specification, but the purpose of the present invention is accomplished using a gene involved in the biosynthesis of arginine derived from other organisms. Therefore, the gene involved in the biosynthesis of arginine is not limited to the genes responsible for the biosynthesis of arginine of Escherichia coli described in the present specification. Further, the vector plasmid merely provides its autonomously replicating ability to stably maintain the recombined gene involved in the biosynthesis of arginine. Therefore, plasmids autonomously replicable in the genus Corynebacterium or Brevibacterium other than pCE53 described in the present specification are used in the present invention.

In spite of many common microbiological properties, microorganisms with high glutamic acid productivity (so-called glutamic acid-producing microorganisms) are classified to various species and even genera such as Corynebacterium and Brevibacterium probably because of their industrial importance. However, it has been pointed out that these microorganisms should be classified as one species because they have homology in the amino acids in the cell walls and the GC content of DNA. Recently, it has been reported that these microorganisms have more than 70% homology in DNA-DNA hybridization, indicating that the microorganisms are very closely related [refer to Komatsu, Y.: Report of the Fermentative Research Institute, No. 55, 1 (1980), and Suzuki, K., Kaneko T., and Komagata, K.: Int. J. Syst. Bacteriol., 31, 131 (1981)].

In the present specification, a case where a gene involved in the biosyntesis of arginine is introduced into Corynebacterium glutamicum ATCC13032, Corynebacterium herculis ATCC13868 and Brevibacterium flavum ATCC 14067 and where the improvement in L-arginine production depends on the expression of the gene is given. Considering the above-mentioned very close relationship of glutamic acid-producing microorganisms, it is readily assumed that the present invention is applicable to all of the glutamic acid-producing microorganisms. The effect of the present invention depends on whether the recombinant DNA autonomously replicates in the glutamic acid-producing microorganism and whether the gene involved in the biosynthesis of arginine is expressed, and so slight difference of such DNA homology between glutamic acid-producing microorganisms are negligible. That the glutamic acid-producing microorganisms have the common function to allow replication of plasmids and expression of genes is apparent from the fact that plasmid pCG4 which is isolated from *Corynebacterium glutamicum* 225-250 (Japanese Published Unexamined Patent Application No. 183799/82) and which has spectinomycin and/or streptomycin resistance gene(s) can be generally replicated and expressed in glutamic acid-producing microorganisms such as strains of the genera Corynebacterium and Brevibacterium (Japanese Published Unexamined Patent Application No. 186492/82). Therefore, all of the glutamic acid-producing microorganisms including the genera Corynebacterium and Brevibacterium such as *Corynebacterium glutamicum* ATCC 13032, *Corynebacterium herculis* ATCC 13868 and *Brevibacterium flavum* ATCC 14067 fall within the scope for application of the present invention to the end that L-argining-producing microorganisms are prepared by introducing a recombinant DNA containing the gene involved in the biosynthesis of arginine.

EXAMPLE 1

(1) In vitro recombination of pLC20-10 and pCE53:

pLC20-10 was isolated from cultured cells of a derivative of *Escherichia coli* K-12 carrying the present plasmid according to the method of An [An, G. et al.: J. Bacteriol., 140, 400 (1979)].

pCE53 was isolated from cultured cells of *Corynebacterium glutamicum* L-22 carrying pCE53 as follows.

The strain was grown in 400 ml of NB medium (pH 7.2) consisting of 20 g/l powdered bouillon and 5 g/l yeast extract to an OD value of about 0.8. Cells were harvested and washed with TES buffer (pH 8.0) consisting of 0.03M tris (hydroxymethyl) aminomethane (referred to as Tris hereinafter), 0.005M EDTA and 0.05M NaCl. The cells were suspended in 10 ml of lysozyme solution (pH 8.0) consisting of 25% sucrose, 0.1M NaCl, 0.05M Tris and 0.8 mg/ml lysozyme and allowed to react at 37° C. for 4 hours. Then 2.4 ml of 5M NaCl, 0.6 ml of 0.5M EDTA (pH 8.0) and 4.4 ml of a solution consisting of 4% sodium lauryl sulfate and 0.7M NaCl were added successively. The mixture was stirred slowly and allowed to stand in an ice water bath for 15 hours. The whole lysate was centrifuged at 4° C. at 69,400× g for 60 minutes. The supernatant fluid was recovered and 10% (by weight) polyethyleneglycol (PEG) 6,000 (product of Nakarai Kagaku Yakuhin Co.) was added. The mixture was stirred slowly to dissolve completely and then kept in an ice water bath. After 10 hours, the mixture was centrifuged at 1,500× g for 10 minutes to recover a pellet. After the pellet was redissolved gently in 5 ml of TES buffer, 2.0 ml of 1.5 mg/ml ethidium bromide was added. Then, cesium chloride was added to adjust the density of the mixture to 1.580. The solution was centrifuged at 18° C. at 105,000× g for 48 hours. After the density gradient centrifugation, a covalently-closed circular DNA was detected under UV irradiation as a high density band located in the lower part of the centrifugation tube. The band was taken out from the side of the tube with an injector to obtain a fraction containing pCE53 DNA. To remove ethidium bromide, the fraction was treated five times with an equal amount of cesium chloride saturated isopropyl alcohol solution consisting of 90% by volume isopropyl alcohol and 10% TES buffer solution. Then, the residue was dialysed against TES buffer solution to obtain pCE53 plasmid DNA.

pCE53 DNA was subjected to single digestion and multiple digestion with various restriction endonucleases and the formed DNA fragments were analyzed by agarose gel electrophoresis to determine the molecular weight and cleavage sites for various restriction enzymes, which are characterized by cleavage map illustrated in FIG. 1.

Five units of PstI (product of Takara Shuzo Co., 5 units/μl) and 5 units of BamHI (product of Takara Shuzo Co., 5 units/μl) were added to 30 μl of PstI-BamHI reaction buffer solution (pH 8.0) consisting of 15 mM Tris-HCl, 10 mM $MgCl_2$, 50 mM NaCl, 25 mM $(NH_4)_2SO_4$, 1 mM mercaptoethanol and 0.01% bovine serum albumin containing 5 μg of pLC20-10 plasmid DNA. The mixture was allowed to react at 33° C. for 90 minutes. Five microgram of pCE53 plasmid DNA was treated by the same method as in the treatment of pLC20-10. Both digests were heated at 65° C. for 10 minutes and mixed. Then, 10 μl of T4 ligase buffer (pH 7.6) consisting of 660 mM Tris-HCl, 66 mM $MgCl_2$ and 100 mM dithiothreitol, 1 μl of 40 mM ATP, 0.3 μl of T4 ligase and 30 μl of $H_2O$ were added to the whole mixture. The reaction was carried out at 4° C. for 12 hours.

(2) Recovery of pEargl:

Transformation was carried out using *Escherichia coli* CH754 which is a derivative of *Escherichia coli* K-12 and requires methionine, tryptophan and arginine (defective mutation of argininosuccinase, argH). Competent cells of CH754 were prepared by the method of Dagert [Dargert, M. et al.: Gene, 6, 23 (1979)]. That is, CH754 strain was inoculated to 50 ml of L-broth (pH 7.2) consisting of 10 g/l Bacto-tryphone, 5 g/l yeast extract, 1 g/l glucose and 5 g/l NaCl and culturing was carried out at 37° C. to an OD value at 660 nm of 0.5 by Tokyo Koden Colorimeter. The culture broth was cooled on an ice water bath for 10 minutes and centrifuged. Cells were suspended in 20 ml of 0.1M $CaCl_2$ cooled and allowed to stand at 0° C. for 20 minutes. Cells recovered by centrifugation were suspended in 0.5 ml of 0.M $CaCl_2$ and allowed to stand at 0° C. for 18 hours. Fifty microliter of ligation mixture obtained above was added to 150 μl of the $CaCl_2$-treated cell suspension. The mixture was allowed to stand at 0° C. for 10 minutes and at 37° C. for 5 minutes. Then 2 ml of L-broth was added and culturing was carried out with shaking at 37° C. for 2 hours. Cells were subjected to washing with physiological saline solution and centrifugation twice. The cells were spread on A agar medium (pH 7.2) consisting of 8 g/l $Na_2HPO_4$, 2 g/l $KH_2PO_4$, 1 g/l $(NH_4)_2SO_4$, 0.1 g/l $MgSO_4.7H_2O$, 4 mg/l thiamine hydrochloride, 10 g/l glucose and 16 g/l agar and containing 40 μg/ml methionine, 40 μg/ml tryptophan and 25 μg/ml kanamycin. Culturing was carried out at 37° C. for 3 days. A plasmid DNA was isolated from cultured cells of a developed transformant by the same method as in the isolation of pLC20-10. The plasmid DNA was digested with restriction endonucleases and analyzed by agarose gel electrophoresis. The plasmid, as illustrated in FIG. 1, has a structure wherein PstI- BamHI fragment containing the genes responsible for the biosynthesis of arginine derived from pLC20-10 and PstI-BamHI fragment containing the gene responsible for kanamycin resistance derived from pCE53 were ligated. The plasmid was named pEargI.

CH754 was retransformed using the plasmid DNA by the same method as described above. Arginine-non-requiring transformants were obtained at a high frequency and all of them were endowed with the phenotype of kanamycin resistance. In the case that *Escherichia coli* CSR603 which is defective in acetylornithine deacetylase (argE) on the pathway of the biosynthesis of arginine and is a derivative of *Escherichia coli* K-12 was transformed, all of the transformants obtained kanamycin resistance were endowed with arginine-non-requiring property.

*Corynebacterium glutamicum* LA291 requiring arginine for its growth was transformed by pEargI. *Corynebacterium glutamicum* LA291 is a mutant which is derived by a conventional mutagenesis from lysozyme-sensitive mutant strain L-15 derived from *Corynebacterium qlutamicum* ATCC 31833 and which requires arginine for its growth. It is assumed that the defective mutation depends on the loss of argininosuccinate synthetase corresponding to argG of *Escherichia coli* or argininosuccinase corresponding to argH of *Escherichia coli* since growth of the mutant does not respond to citrulline which is a precursor two steps before arginine on the pathway of arginine biosynthesis. A seed culture of *Corynebacterium qlutamicum* LA291 was inoculated in NB medium and culturing was carried out with shaking at 30° C. Cells were harvested at an OD value of 0.6 and suspended in an RCGP medium (pH 7.6) containing 1 mg/ml lysozyme at a concentration of about $10^9$ cells/ml. The RCGP medium consists of 5 g/l glucose, 5 g/l casamino acid, 2.5 g/l yeast extract, 3.5 g/l $K_2HPO_4$, 1.5 g/l $KH_2PO_4$, 0.41 g/l $MgCl_2.6H_2O$, 10 mg/l $FeSO_4.7H_2O$, 2 mg/l $MnSO_4.(4-6) H_2O$, 0.9 mg/l $ZnSO_4.7H_2O$, 0.04 mg/l $(NH_4)_6Mo_7O_{24}.4H_2O$, 30 μg/l biotin, 2 mg/l thiamine hydrochloride, 135 g/l sodium succinate and 30 g/l polyvinylpyrrolidone of a molecular weight of 10,000. The suspension was put into an L-tube and allowed to react with gentle shaking at 30° C. for 5 hours to make protoplasts.

Then, 0.5 ml of the protoplast suspension was transferred into a small tube and centrifuged at 2,500× g for 5 minutes. The pellet was resuspended in 1 ml of TSMC buffer solution (pH 7.5) consisting of 10 mM magnesium chloride, 30 mM calcium chloride, 50 mM Tris and 400 mM sucrose and centrifuged. The protoplasts were resuspended in 0.1 ml of TSMC buffer solution. Then, 100 μl of a mixture of a two-fold concentrated TSMC buffer solution and the pEargI plasmid DNA solution (1:1) was added to the suspension and 1.0 ml of TSMC buffer solution containing 20% PEG 6,000 was added. After 3 minutes, the mixture was centrifuged at 2,500× g for 5 minutes, and the supernatant fluid was removed. The precipitated protoplasts were suspended in 1 ml of RCGP medium (pH 7.4), and the suspension was slowly shaken at 30° C. for 2 hours. Then, 0.3 ml of the protoplast suspension was spread on RCGP agar medium (pH 7.4), i.e. the RCGP medium supplemented by 1.6% agar, containing 400 μg/ml kanamycin, and culturing was carried out at 30° C. for 6 days.

All of the developed kanamycin-resistant transformants were endowed with arginine-nonrequiring property.

A plasmid DNA was isolated from cultured cells of the transformant by the same method as in the isolation of pCE53. The plasmid was digested with restriction endonucleases and analyzed by agarose gel electrophoresis to determine that the plasmid has the same structure as pEargI characterized by the cleavage pattern for various restriction endonucleases.

(3) Production of L-arginine by the pEargI-carrying strains:

*Corynebacterium glutamicum* ATCC 13032, *Corynebacterium herculis* ATCC 13868 and *Brevibacterium flavum* ATCC 14067 were transformed with pEargI. The strains were cultured with shaking in NB medium at 30° C. for 16 hours, and 0.1 ml of the seed culture was inoculated into 10 ml of SSM medium (pH 7.2) consisting of 10 g/l glucose, 4 g/l $NH_4Cl$, 2 g/l urea, 1 g/l yeast extract, 1 g/l $KH_2PO_4$, 3 g/l $K_2HPO_4$, 0.4 g/l $MgCl_2.6H_2O$, 10 mg/l $FeSO_4.7H_2O$, 0.2 mg/l $MnSO_4.(4-6)H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 30 μg/l biotin and 1 mg/l thiamine hydrochloride in an L-tube. Culturing was carried out at 30° C. in a Monod-type culture bath, and penicillin G was added at an OD value of 0.15 to a concentration of 0.5 unit/ml. Culturing was continued to an OD value of about 0.6. Cells were harvested and suspended in 2 ml of RCGP medium (pH 7.6) containing 1 mg/ml lysozyme. The suspension was put in an L-tube and stirred slowly at 30° C. for 14 hours to obtain protoplasts.

Then, 1 ml of the protoplast suspension was put in a small test tube and centrifuged at 2,500× g for 15 minutes. The protoplasts were resuspended in 1 ml of TSMC buffer and again subjected to centrifugation at 2,500× g and washing. The washed protoplasts were resuspended in 0.1 ml of TSMC buffer solution. One hundred microliter of a mixture (1:1 by volume) of a two-fold concentrated TSMC buffer and the pEargI DNA mixture described above was added to the protoplast suspension. Transformation was carried out using PEG 6,000 by the same method described in Example 1 (2) for expression of the desired gene. Then, 0.3 ml of the mixture was spread on RCGP agar medium containing 400 μg/ml kanamycin and incubated at 30° C. for 10 days. Kanamycin-resistant strains were cultured with shaking in 400 ml of SSM medium, and penicillin G was added at an OD value of 0.15 to a concentration of 0.5 unit/ml. Culturing was continued to an OD value of 0.65, and cells were harvested. From the cells, plasmids were isolated by the same method as the isolation method of pCE53 in Example 1 (1). These plasmids were digested with restriction endonucleases and analyzed by agarose gel electrophoresis. The analysis showed that the plasmids have the same structure as pEargI characterized by the cleavage pattern for various restriction endonucleases. Such transformants are *Corynebacterium qlutamicum* K-46 (FERM BP-356), *Corynebacterium herculis* K-47 (FERM BP-367) and *Brevibacterium flavum* K-48 (FERM BP-357).

*Corynebacterium glutamicum* ATCC 13032, *Corynebacterium herculis* ATCC 13868, *Brevibacterium flavum* ATCC 14067 and their pEargI-carrying strains were tested for L-arginine production as follows.

The strains were cultured with shaking in NB medium at 30° C. for 16 hours and 0.5 ml of the seed culture was inoculated in a production medium (pH 7.0) consisting of 80 g/l molasses (as glucose), 40 g/l $(NH_4)_2SO_4$, 0.5 g/l $KH_2PO_4$, 0.5 g/l $K_2HPO_4$, and 20 g/l CaCO₃. Culturing was carried out with shaking at 30° C. for 72 hours. The culture filtrate was subjected to paper chromatography, color reaction with ninhydrin and the amount of L-arginine formed was determined colorimetrically. The results are shown in Table 1.

TABLE 1

| Strain | Amount of L-arginine (mg/ml) |
|---|---|
| *Corynebacterium glutamicum* ATCC 13032 | 0 |
| *Corynebacterium glutamicum* K-46 | 1.6 |
| *Corynebacterium herculis* ATCC 13868 | 0 |
| *Corynebacterium herculis* K-47 | 1.8 |
| *Brevibacterium flavum* ATCC 14067 | 0 |
| *Brevibacterium flavum* K-48 | 1.0 |

What is claimed is:

1. A process for producing L-arginine which comprises the steps of transforming a host microorganism belonging to the genus Corynebacterium or Brevibacterium with a vector containing a DNA fragment comprising an *Escherichia coli* gene coding for N-acetyl-glutamokinase, culturing the transformant in a nutrient medium, accumulating L-arginine in the culture medium an recovering L-arginine therefrom.

2. A process for producing L-arginine which comprises the steps of culturing a Corynebacterium or Brevibacterium host microorganism harboring a vector containing a DNA fragment comprising an *Escherichia coli* gene coding for N-acetylglutamokinase in a nutrient medium, accumulating L-arginine in the culture medium and recovering L-arginine therefrom.

3. A microorganism belonging to the genus Corynebacterium or Brevibacterium which harbors a vector containing a DNA fragment comprising an *Escherichia coli* gene coding for N-acetyl-glutamokinase.

4. *Corynebacterium glutamicum* K-46 (FERM BP-356).

5. *Corynebacterium herculis* K-47 (FERM BP-367).

6. *Brevibacterium flavum* K-48 (FERM BP-357).

* * * * *

UNITED STATES PATENT AND TRADEMARK OFFICE
CERTIFICATE OF CORRECTION

PATENT NO. : 4,775,623

DATED : October 4, 1988

INVENTOR(S) : RYOICHI KATSUMATA, ET AL.

It is certified that error appears in the above-identified patent and that said Letters Patent is hereby corrected as shown below:

Cover Page, at [73] "Kyowa Khkko Kogyo Co., Ltd.," should read --Kyowa Hakko Kogyo Co., Ltd.,--.

Column 12, line 4, "an" should read --and--.

Signed and Sealed this

Thirty-first Day of January, 1989

Attest:

DONALD J. QUIGG

Attesting Officer     Commissioner of Patents and Trademarks